United States Patent
Kowalsky et al.

[11] Patent Number: 6,127,063
[45] Date of Patent: Oct. 3, 2000

[54] INTELLIGENT BATTERY AND WELL INTERFACE

[75] Inventors: Leonard W. Kowalsky; Rodney J. Merry, both of Woodinville; John C. Daynes, Redmond; Douglas J. Hill, Newcastle; Judith F. Marquardt, Arlington, all of Wash.

[73] Assignee: Physio-Control Manufacturing Corporation, Redmond, Wash.

[21] Appl. No.: 09/013,569

[22] Filed: Jan. 26, 1998

[51] Int. Cl.⁷ ...................................................... H01M 2/10
[52] U.S. Cl. .............................. 429/100; 429/96; 429/97; 429/99
[58] Field of Search ..................................... 429/151, 159, 429/163, 177, 96, 97, 99, 100; 607/5

[56] References Cited

U.S. PATENT DOCUMENTS

| | | |
|---|---|---|
| D. 278,426 | 4/1985 | Lanci et al. . |
| D. 322,853 | 12/1991 | Benson et al. . |
| 5,078,615 | 1/1992 | Benson et al. . |
| 5,415,955 | 5/1995 | Kobayashi et al. .................. 429/97 |
| 5,432,017 | 7/1995 | Hassemer et al. ..................... 429/4 |
| 5,466,545 | 11/1995 | Chamberlain et al. ................ 429/99 |

OTHER PUBLICATIONS

LIFEPACK® 10 product brochure, Physio–Control Corporation, 1995. (month not available).
STREET SMART® product brochure, Physio–Control Corporation, 1995. (month not available).

*Primary Examiner*—Maria Nuzzolillo
*Assistant Examiner*—Raymond Alejandro
*Attorney, Agent, or Firm*—Christensen O'Connor Johnson Kindness PLLC

[57] ABSTRACT

A battery (10) contains a base portion (12) that is shaped generally rectangular parallelpiped. The bottom face (18) of the base portion (12) contains a raised notch portion (22) at the first end (14) of the base portion directly beneath an upper ledge (20) that extends along the perimeter of the first end. The first end (14) contains two keyed recesses (24) that extend from an upper ledge (20) to the notch portion (22) of the bottom face (18). A blade connector (26) is located between the two keyed recesses (24) at the intersection of the notch portion (22) and the first end (14). The bottom face (18) contains two apertures (28) for receiving pin shaped positive and negative cell terminals. The second end (16) contains a resiliently attached latch member (30). A corresponding battery well (40) contains opposite first and second ends (44) and (46), a bottom floor (48), and a rim portion (50) that extends along the first end. The bottom floor (48) contains a raised step portion (52) located directly beneath the overhanging rim (50) at the first end. The first end (44) contains two protrusions (54) that span from the step portion (52) to the overhanging rim (50). A blade connector (56) is located on the step portion (52) between the two protrusions (54) at the first end (44). The bottom floor (48) contains two banana plug cell terminals (58), near the second end (46). Three retractable contact pins (60) are aligned between the two banana plug cell terminals (58) in the bottom floor (48). The second end (46) contains an overhanging flange (62) that is bisected by a central indentation (64).

34 Claims, 10 Drawing Sheets

INTELLIGENT BATTERY AND WELL INTERFACE

FIELD OF THE INVENTION

The invention generally relates to power supplies for portable defibrillators, and more specifically to batteries and battery wells for portable defibrillators and related battery charging units.

BACKGROUND OF THE INVENTION

The probability of surviving a heart attack in large part depends on the speed with which appropriate medical care is provided to the person experiencing the heart attack. The response time to a patient suffering a heart attack, can be decreased if those persons who are typically first to arrive at the scene of a medical emergency, including emergency medical technicians (EMTs), firefighters, the police, and even the public (hereinafter collectively referred to as "first responders") are provided with portable defibrillators. A first responder equipped with a portable defibrillator will have a greater likelihood of successfully treating the patient than those who arrive later at the scene. A defibrillator designed for first responder use would therefore improve the overall success rate of treating heart attack patients.

All defibrillators must contain or be connected to an energy source to generate and apply a defibrillation pulse to the patient. For true portability, most portable defibrillators are constructed with a battery pack that is of sufficient capacity to operate the portable defibrillator for a period of time. The battery pack may be either rechargeable or non-rechargeable, depending on the user's preference and the environment in which the defibrillator is to be used. Rechargeable battery packs typically power a defibrillator for a shorter period of time than non-rechargeable battery packs, but can be recharged and reused. In contrast, non-rechargeable battery packs allow the defibrillator to operate for a longer period but require replacement when the battery pack is discharged.

A portable defibrillator is unusable as a medical treatment device without the battery pack or with a battery pack that is discharged. It should therefore be very easy for the first responder to remove and replace the battery pack to ensure that the defibrillator is always available for use. In most situations, changing the battery pack will typically occur during normal testing of the defibrillator in a non-emergency setting. Occasionally, however, a first responder may have to change the battery pack at the site of the emergency. For example, a prior user of the defibrillator could have left a discharged battery pack in the device and that situation is not discovered until treatment is to be initiated on a patient. Alternatively, the battery pack could become fully discharged when the defibrillator is in use, requiring the first responder to replace the battery pack before continuing treatment. To speed the changing of battery packs, it would therefore be desirable to make the changing process as simple and intuitive as possible.

Unfortunately, the replacement of many prior art battery packs in portable defibrillators has not been very straightforward. For example, the correct orientation to insert the battery pack into the portable defibrillator often has not been readily apparent from the shape of the battery pack. Further, to properly connect the battery pack to the defibrillator often has required a precise alignment of sockets in the battery pack with conductive pins in the defibrillator. If the pins were not properly aligned as the battery pack was being inserted into the defibrillator, the user ran the risk of bending and/or breaking the pins. Moreover, prior art battery packs often did not easily latch into the defibrillator. Without a positive and simple latching mechanism to secure the battery pack to the portable defibrillator, a user had to be careful when installing the battery pack to ensure that it was appropriately attached to the device.

All of the above disadvantages of prior art battery packs have combined to make it difficult to replace a battery pack in a portable defibrillator, a task that usually required a user to use both hands when performing the replacement. The present invention is directed to overcoming the foregoing and other disadvantages. More specifically, the present invention is directed to an improved battery and battery well design that helps facilitates easy insertion by a first responder of a battery into a portable defibrillator or charging unit.

SUMMARY OF THE INVENTION

The present invention teaches a battery and a corresponding battery well. The battery disclosed contains a base portion that is generally in the shape of a rectangular parallelpiped. The base portion has a first end, a second end, a bottom face that spans between the first and second ends, and an upper ledge that extends along the perimeter of the first end of the base portion opposite the bottom face. The first end of the battery base portion contains at least one keyed recess. The base portion has a shape and length such that the at least one keyed recess is configured to mate with at least one corresponding protrusion in the corresponding battery well. The upper ledge of the battery base portion is formed to be closely receivable under an overhanging rim portion of the corresponding battery well.

The battery well disclosed contains a cavity that is formed in generally the shape of a rectangular parallelpiped. The well has a first end, a second end, a bottom floor that spans between the first and second ends, and an overhang that extends along the first end of the well to define a rim portion. The first end of the battery well contains at least one protrusion. The well is capable of accepting the above described first battery that has at least one corresponding recess formed in the battery base portion, such that the recess is configured to mate with the at least one protrusion of the battery well. The well is also capable of accepting a differing second battery that has a shorter length than the first battery and a substantially flat ended first end, such that the substantially flat first end of the battery is configured to abut against the at least one protrusion of the battery well. The overhanging rim portion of the battery well is positioned such that the upper ledge of the battery base portion is closely receivable under the rim portion.

In an actual embodiment of the present invention three battery wells are utilized in side-by-side arrangement in a battery charging unit. The battery wells are shaped generally rectangular parallelpiped and are positioned next to each other with only a small dividing rib between each well. Each well has a first end that contains two protrusions which extend outwards towards the opposite second end of each well. The first end of each well further contains an overhanging rim that also extends outward towards the opposite second end of each well. The width of each protrusion is a significant portion of the width of the overhanging rim, but does not extend beyond the overhanging rim. A blade connector is located between the two protrusions in each well, on the bottom floor of each well directly underneath the overhanging rim. The bottom floor of each well further contains a banana plug cell terminal at each end of three linearly aligned retractable pin-shaped contacts. All five pins are arranged parallel to and located near the second end of each well.

In another actual embodiment of the present invention two battery wells are utilized in end-to-end arrangement in a portable defibrillator unit. This end-to-end configuration places the first end of each battery well, which contains the two outwardly extending protrusions and the blade connector, next to each other and the second end of each well at the outer perimeter. Although the bottom floor of each battery well contains two banana plug terminals near the second ends, the floors of the wells do not contain the three retractable pin-shaped contacts. In all other aspects, the battery wells of the portable defibrillator are the same as the battery wells of the charging unit.

In an actual embodiment battery of the present invention, the battery includes a base portion that is shaped generally rectangular parallelpiped. The battery base portion has a first end that includes two keyed recesses which are designed to mate with the two corresponding protrusions in the battery wells of compatible portable defibrillators and charging units. Each keyed recess is channel-shaped with outwardly sloping sidewalls and which run the entire height of the base portion at the first end. The battery base portion further includes an upper ledge that extends along the perimeter of the first end of the base portion and contains the two keyed recesses. The upper ledge is configured to be closely receivable under the overhanging rim of the corresponding battery wells. A blade connector is located between the two keyed recesses in the first end of the battery base portion and is configured to interface with a corresponding blade connector in a compatible battery well. The bottom face of the battery base portion contains two apertures which are sized to receive pin-type terminal connectors from a corresponding battery well.

The utilization of batteries and battery wells constructed in accordance with the present invention helps to facilitate proper insertion of batteries into only compatible battery wells of portable defibrillators and charging units by way of their uniquely matable configuration. The battery is shaped such that it will not fit into a non-compatible battery well of a charging unit or portable defibrillator, which would damage the battery and the unit to which the battery was attached. The battery well however, is configured such that the well will ideally receive a corresponding battery that contains compatible keyed recesses and accessible electronic connectors, but will also be backwardly compatible such that a battery of an older configuration can still be utilized in an emergency or otherwise non-ideal situation.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
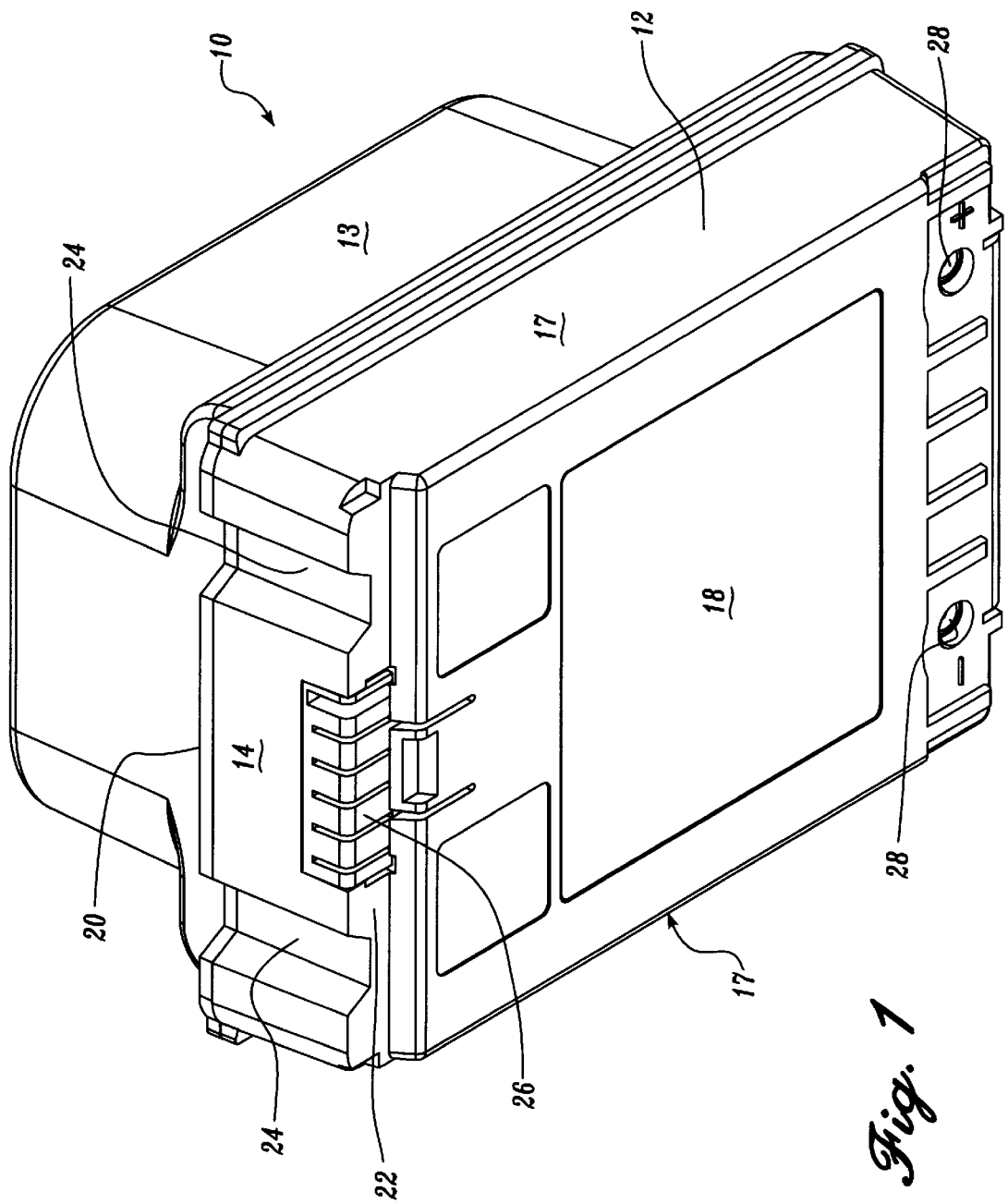
FIG. 1 illustrates a bottom perspective view of an actual embodiment battery (first battery) of the present invention having two keyed recesses in its first end.
Figure 2:
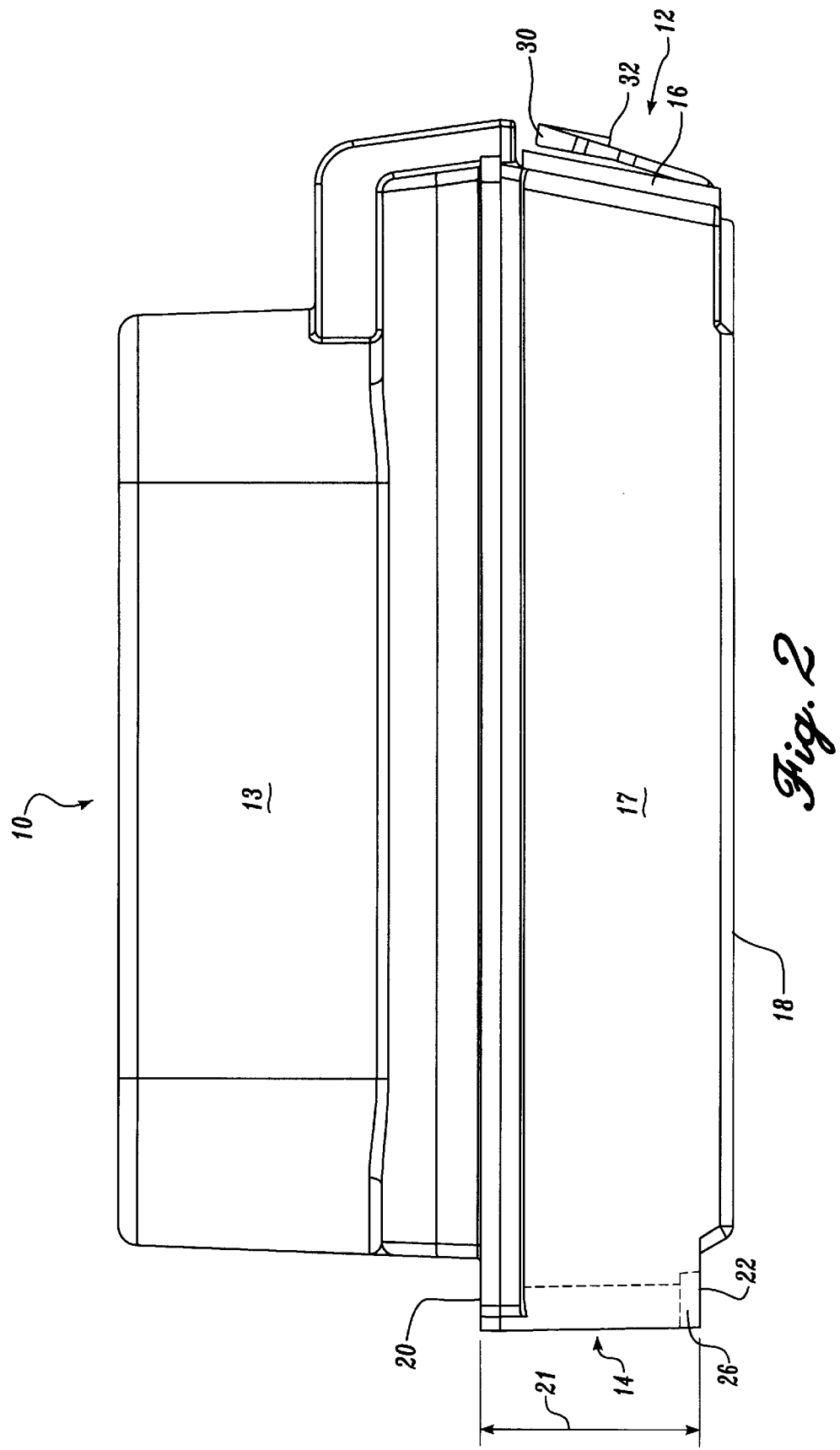
FIG. 2 illustrates a side view of an actual embodiment battery (first battery) of the present invention having at least one keyed recess in its first end.
Figure 3:
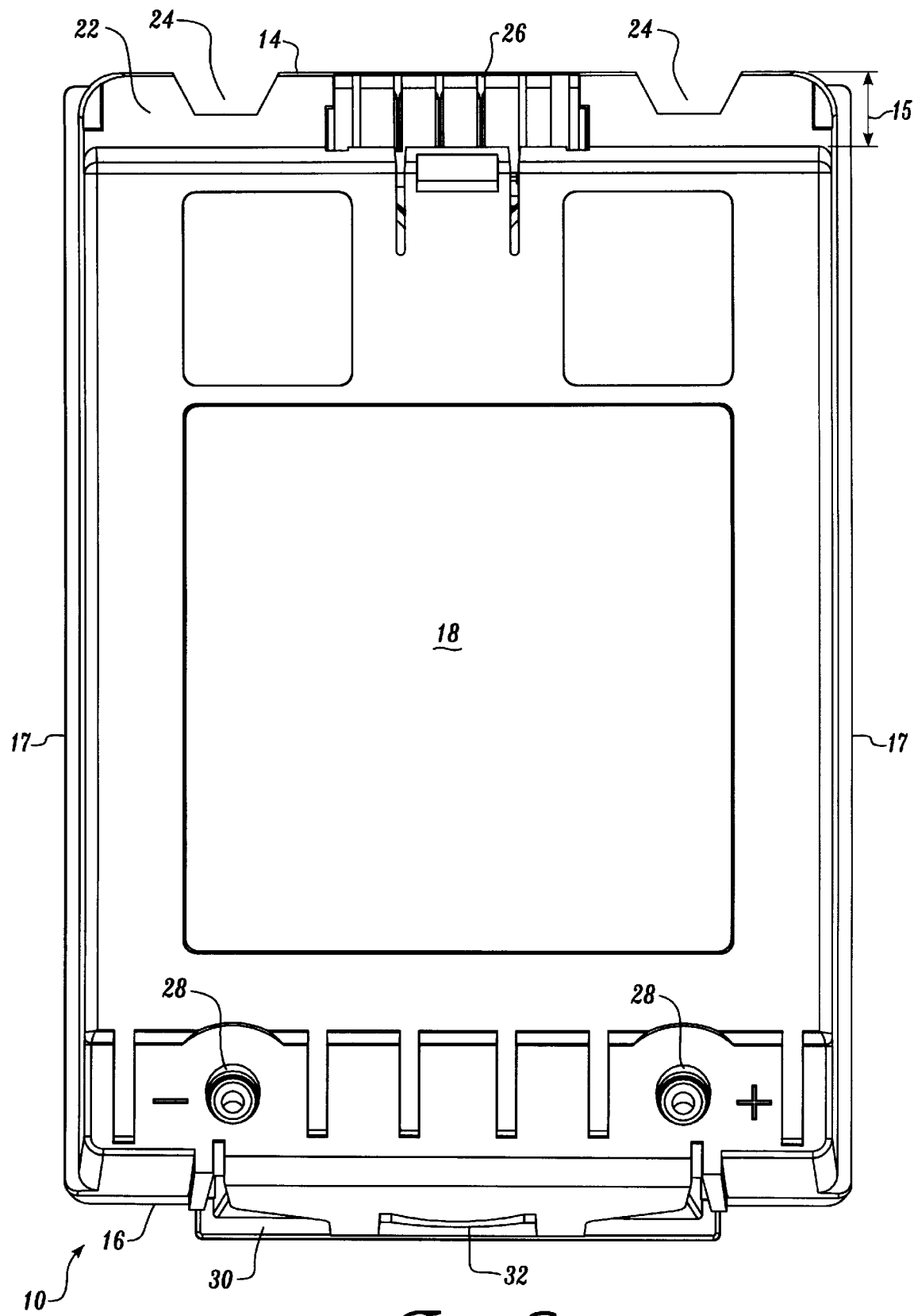
FIG. 3 illustrates a bottom view of an actual embodiment battery (first battery) of the present invention having two keyed recesses in its first end.

FIGS. 1–3 illustrate a preferred embodiment of a battery 10 constructed in accordance with the present invention. The battery 10 has a base portion 12 that is generally in the shape of a rectangular parallelpiped. The base portion 12 has opposite first and second ends 14 and 16, and sides 17. In addition, the base portion 12 includes a bottom face 18 that extends between the first and second ends 14 and 16, and between the sides 17. The base portion 12 also includes an upper ledge 20 that extends along the perimeter of the first end 14 of the base portion 12 opposite the bottom face 18. The bottom face 18 contains a raised notch portion 22 at the first end 14 of the base portion 12 directly beneath the upper ledge 20. Two keyed recesses 24 are formed in the first end 14 of the battery base portion 12. The keyed recesses 24 are in the shape of vertical channels and extend from the upper ledge 20 down to the notch portion 22. A blade electrical connector 26 is located between the two keyed recesses 24 at the intersection of the notch portion 22 and the first end 14 of the battery base portion 12. The bottom face 18 further defines two circular apertures 28 located near the second end 16 of the base portion 12 for receiving pin shaped positive and negative cell terminals. The second end 16 of the base portion 12 further includes a resiliently attached latch member 30. A lip 32 is formed at the distal end of the latch member 30.

Figure 4:
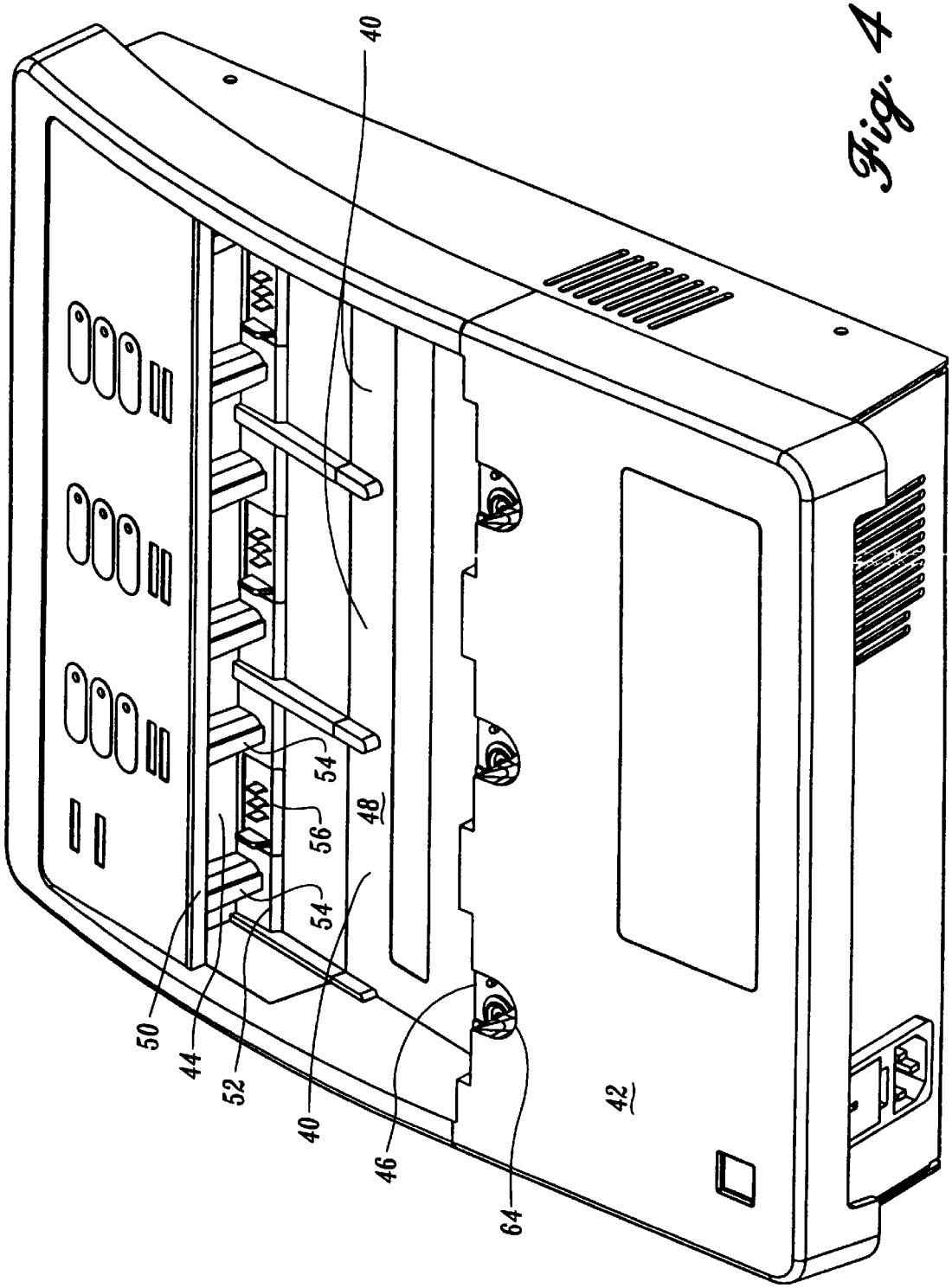
FIG. 4 illustrates a perspective view of an actual embodiment of a charging unit having three battery wells in side-by-side alignment, with the first ends of the battery wells in view.
Figure 5:
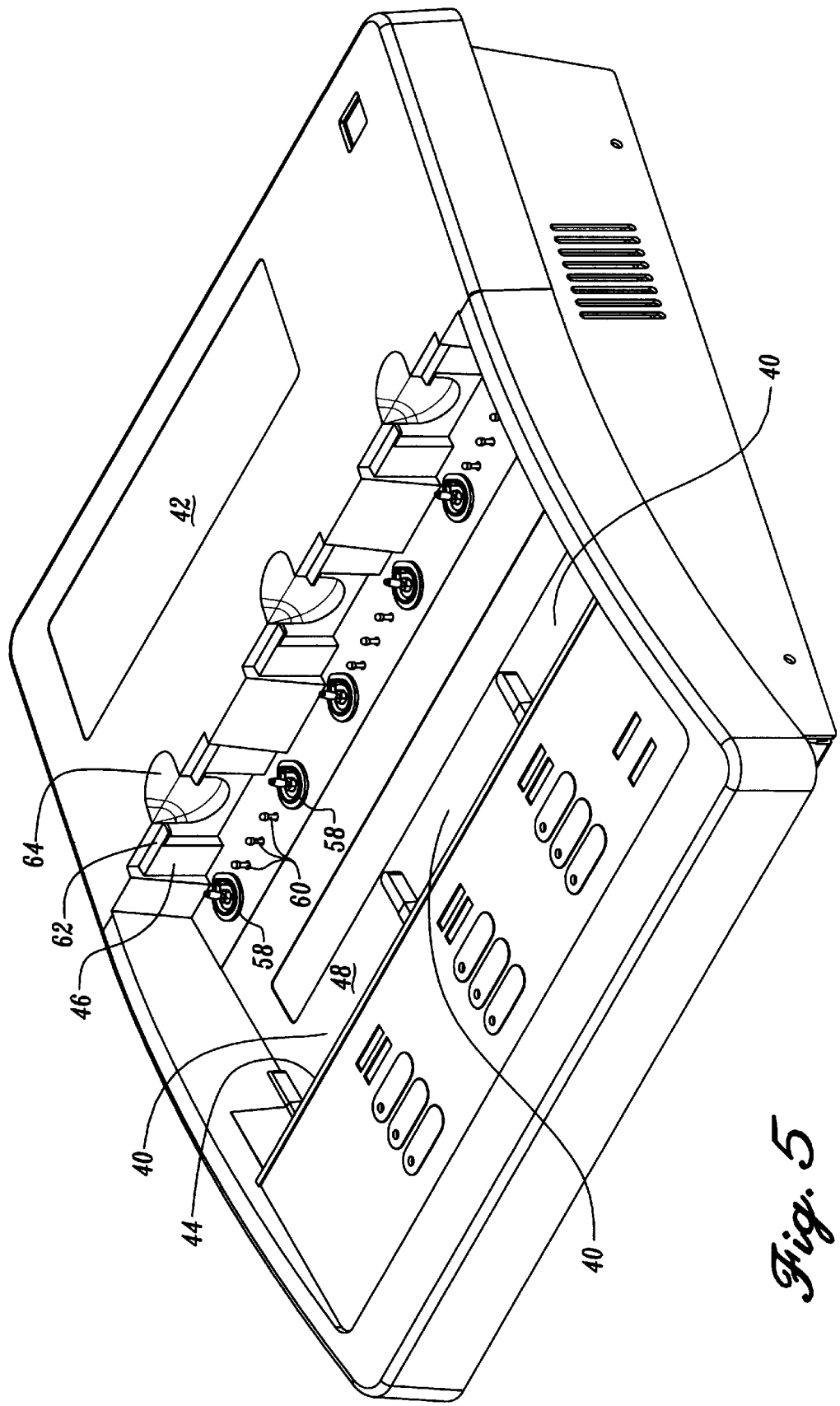
FIG. 5 illustrates a perspective view of the charging unit of FIG. 4 with the second ends of the battery wells in view.
Figure 6:
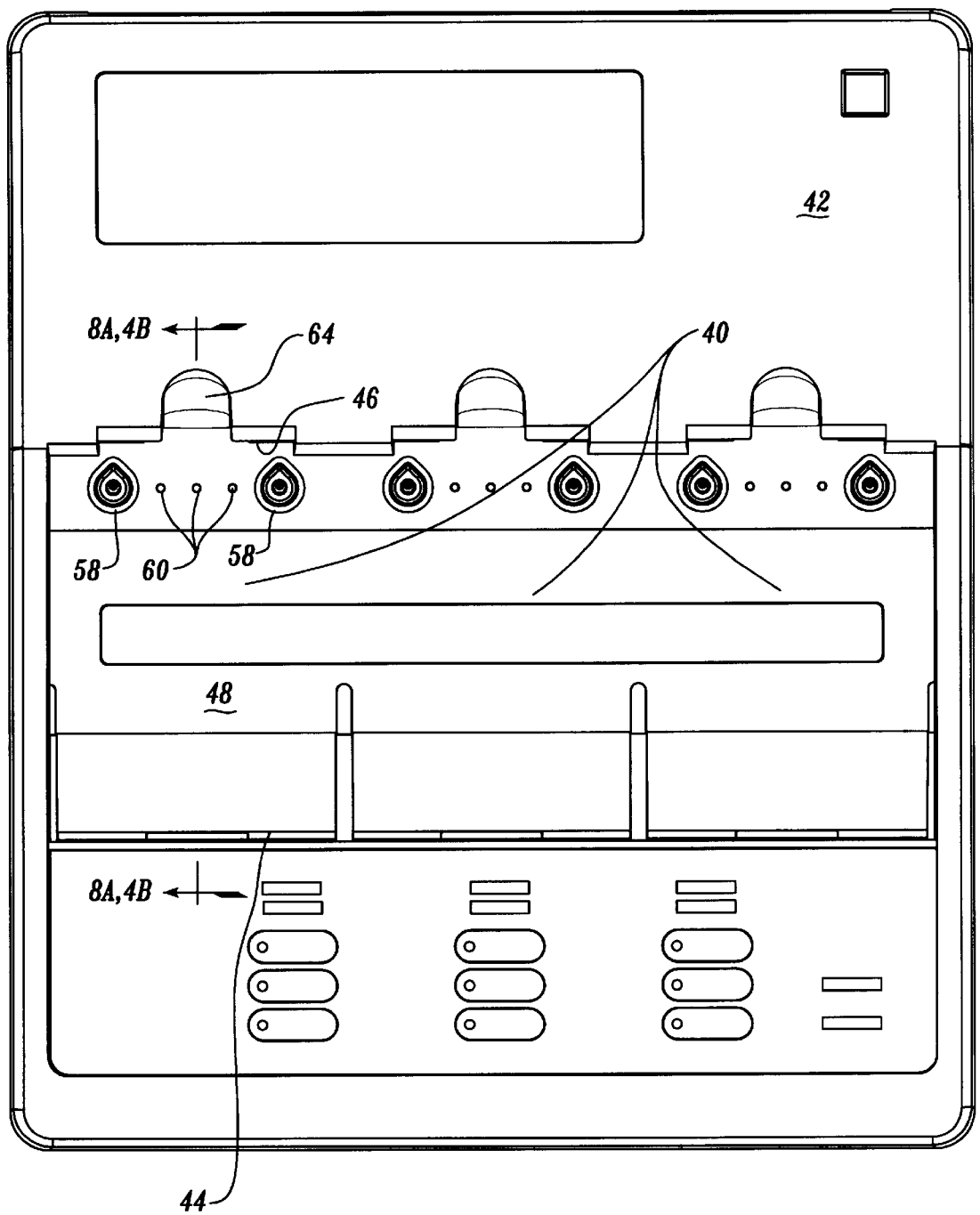
FIG. 6 illustrates a top view of the battery charging unit of FIGS. 5 and 6.

FIGS. 4–6 illustrate a battery charging unit 42 constructed with three battery wells 40 arranged in a side-by-side configuration across the charging unit. The battery wells 40 are shaped generally in the form of a rectangular parallelpiped and are positioned directly side-by-side to one another with only small rail guides between them. Each battery well 40 contains opposite first and second ends 44 and 46, a substantially flat bottom floor 48 that extends between the first and second ends 44 and 46, and an overhang that extends along the first end 44 to define a thin rim portion 50. The bottom floor 48 is formed with a raised step portion 52 located substantially directly beneath the overhanging rim 50 at the first end 44 of each battery well 40. Each first end 44 further includes two protrusions 54 that extend into the well 40 toward the second end 46 and span vertically from the step portion 52 to the under side of the overhanging rim 50. A blade connector 56 is located on the step portion 52 between the adjacent two protrusions 54. Two circular banana plug cell terminals 58, extend upwardly from the bottom floor 48 near the second end 46 of each well 40. Three retractable contact pins 60 also extend upwardly from the bottom floor 48 in alignment with and between the two banana plug cell terminals 58 of each battery well 40. The second end 46 of each battery well 40 contains an overhanging flange 62 that has been bisected by a central indentation 64 generally in the shape of a sphere segment.

Figure 7:
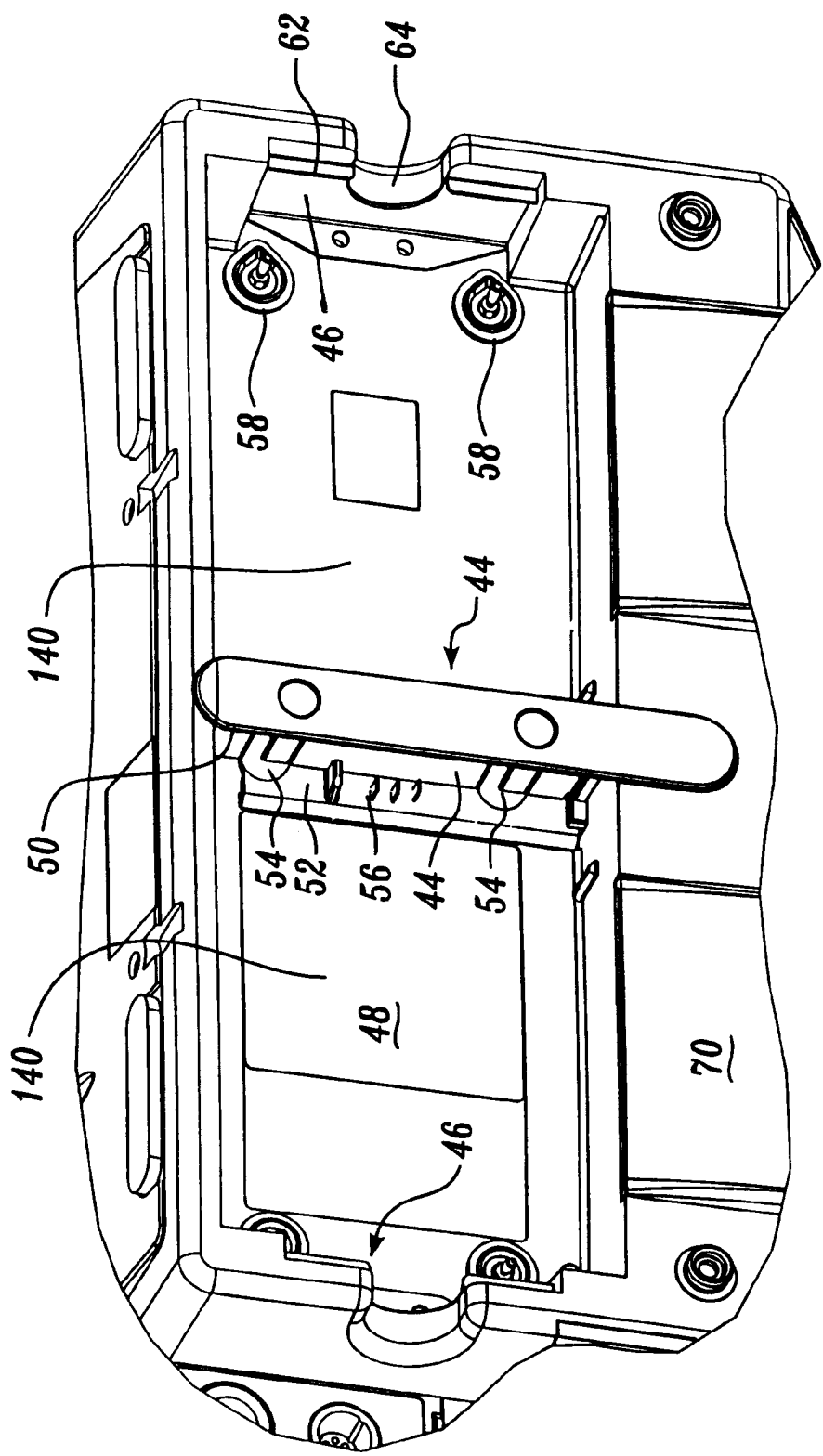
FIG. 7 illustrates an partial bottom perspective view of a portable defibrillator unit having two battery wells in end-to-end alignment.

FIG. 7 illustrates a portion of a portable defibrillator unit 70 utilizing two battery wells 140 in an end-to-end arrangement. The end-to-end configuration implemented in the portable defibrillator 70 places the first ends 44 of the battery wells 140 (which contain the overhanging rim 50, the step portion 52, the two outwardly extending protrusions 54, and the blade connector 56), centrally next to each other so that the second ends 46 of the wells 140 are located at the far end of the respective wells. The two banana plug cell terminals 58, are positioned in the bottom floor 48 of each battery well 140 of the portable defibrillator 70, but the three retractable contact pins 60 are not used. However, it will be appreciated by those of ordinary skill in the art that in other embodiments of the present invention, the battery wells 140 do include the retractable contact pins 60. The battery wells 140 of the portable defibrillator 70 preferably are the same as the battery wells 40 of the charging unit 42 in all other aspects, and as such both battery wells 40 and 140 will be referred to as battery wells 40, unless the battery wells 140 are being specifically individually addressed.

Referring again to FIG. 1, the battery 10 is shown to have a bulbous upper section 13 that extends upwardly from the base portion 12. The particular configuration of the upper section 13 of the battery 10 is greatly determined by the chemistry of the battery. Both the configuration of the upper section 13 and the chemistry of the battery 10 can be varied without departing from the scope of the present invention. The configuration and length of the battery base portion 12 are the most important features of the battery 10.

Figure 8A:
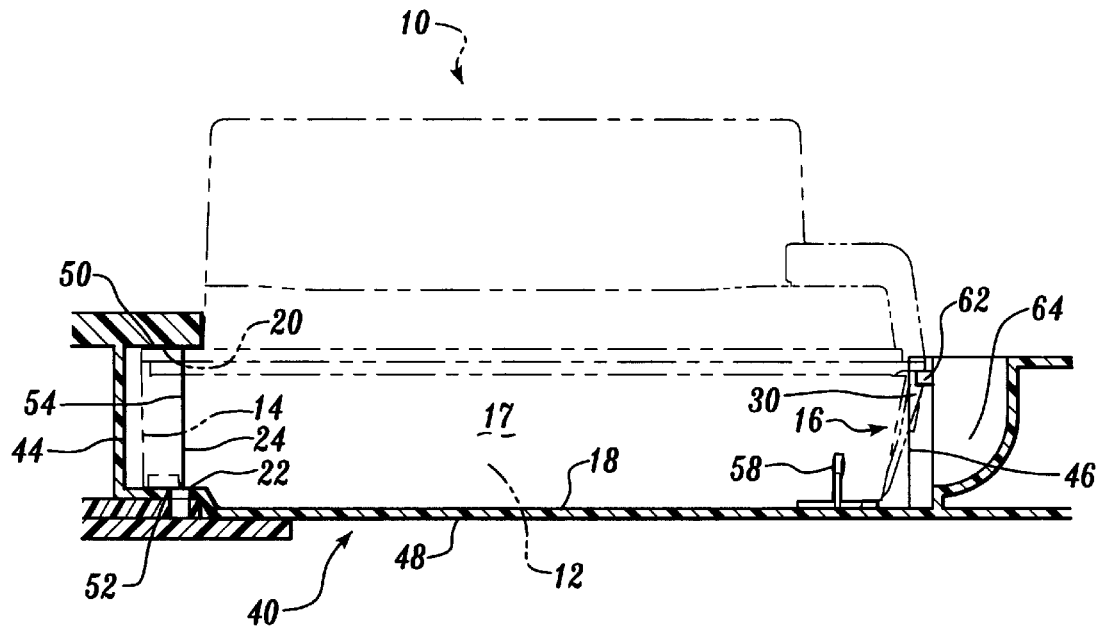
FIG. 8A illustrates a side cross-sectional view of an actual embodiment battery well and a first battery drawn in phantom, with the battery positioned in the battery well such that the at least one protrusion in the first end of the battery well is mated with the at leas one keyed recess in the first end of the battery.

The first end 14 of the battery base portion 12 contains several important features, which can be seen in FIGS. 1 and 2. The top of the first end 14 is bounded by an upper ledge 20 which forms the upper surface of the battery base portion 12 and runs the entire width of the first end 14. The bottom of the first end 14 is bounded by a notch portion 22 extending upwardly from the bottom face 18 of the base portion 12. The notch portion 22 also runs across the entire width of the first end 14 and is substantially parallel to the upper ledge 20 of the battery base portion 12. The notch portion 22 is of substantially the same width 15 as the upper ledge 20. The notch portion 22 intersects the bottom face 18 of the base portion 12 at an angle of approximately 45°. Referring to FIG. 2, the distance (height 21) between the upper ledge 20 and the notch portion 22 of the battery base portion 12 is important. This portion of the battery base 12 is designed to be closely receivable between the overhanging rim 50 and the step portion 52 at the first end 44 of a corresponding battery well 40, as can be seen in FIG. 8A. An incompatible battery without a first end of this dimension and configuration will be prevented from properly nesting in the battery well 40 by the overhanging rim 50 and/or the step portion 52.

As shown in FIG. 1, the first end 14 of the battery base portion 12 further contains two keyed recesses 24. Each recess is generally channel-shaped and spans vertically across the entire first end 14 from the notched portion 22 to the upper ledge 20. The sidewalls of each channel-shaped keyed recess 24 are outwardly sloping in the direction out of or away from the bottom of the recess. As perhaps best illustrated in FIG. 3, the two keyed recesses 24 extend into the base portion 12 towards the opposite second end 16 of the battery 10. This "depth" of the two keyed recesses 24 constitutes a significant portion of the widths 15 of the upper ledge 20 and the notch portion 22 of the battery base portion 12.

Referring again to FIG. 1, a blade connector 26 is located at the lower center of the first end 14 between the two keyed recesses 24 to intersect the center notice portion 22. The two keyed recesses 24 preferably are symmetrical about the blade connector 26 in the first end 14 of the base portion 12. The battery 10 is an "intelligent" battery, containing electronic circuitry which controls the charging, conditioning, and other features of the battery. This electronic circuitry in the battery 10 communicates with the electronic circuitry in a compatible charging unit 42 or portable defibrillator 70 through the blade connector 26 which interfaces with a corresponding blade connector 56 in a compatible battery well 40. The location of the blade connector 26 at the intersection of the first end 14 and the notch portion 22 of the base portion 12 must be such that the blade connector 56 mates with the corresponding blade connector 56 of the compatible battery well 40.

The two apertures 28 contained in the bottom face 18 of the base portion 12 near the second end 16 of the battery, are necessary for proper functioning of the battery. These two apertures 28 are designed to receive two banana plug terminals 58 which are located in the bottom floor 48 of a corresponding battery well 40. The inside of the two apertures 28 contain conductive contacts to the positive and negative terminals of the battery cell. The conductive contacts located within the two apertures 28 provide the conduit through which the battery 10 receives charge from the charging unit 42 and provides charge to the portable defibrillator 70.

Referring again to FIG. 2, a latch or lever member 30 is located in the center of the second end 16 of the battery base portion 12. The latch member 30 is resiliently attached to the battery base portion 12 at the intersection of the second end 16 and the bottom face 18. From this attachment point, the latch member 30 extends upwardly and slightly outwardly from the second end 16. The free end of the latch member 30 terminates near the top of the second end 16 of the base portion 12. The latch member 30 nominally protrudes from the base portion in its free extended position. The latch member 30 can be pushed into its retracted position towards the second end 16 by way of finger pressure to a position adjacent the second end 16. The distal surface of the latch member 30 is in the shape of a lip 32. When the battery 10 is placed into the corresponding battery well 40, the latch member 30 hooks underneath the overhanging flange 62 in the second end 46 of the corresponding battery well 40 to lock the battery 10 in place in the battery well. The latch member 30 can be accessed through the central indentation 64 in the second end 46 of the corresponding battery well 40 and pushed into its retracted position so that the latch member 30 unhooks from the overhanging flange 62. The distal lip 32 then provides a gripping edge to assist in the removal of the battery 10 from the well 40.

Referring to FIGS. 4–7, the three side-by-side arranged battery wells 40 of the charging unit 42 and the two end-to-end arranged battery wells 140 of the portable defibrillator 70 are uniquely configured to accept the above-described battery 10 and secure it in place. Since the battery wells 40 of the charging unit 42 are nearly identical to the battery wells 140 of the portable defibrillator 70, the description of the battery well 40 will also apply to the battery well 140 unless otherwise specifically noted.

As shown in FIGS. 4 and 7, the configuration of the first end 44 of each battery well 40 is important to proper compatibility with corresponding batteries. The first end 44 of each battery well 40 contains an overhanging rim 50 that extends outward towards the opposite second end 46 of each battery well 40. Directly underneath the overhanging rim 50 is a raised step portion 52 in the bottom floor 48 of the well 40. The step portion 52 intersects the bottom floor 48 of the battery well 40 at an angle of approximately 45°. This angled slope of the step portion 52 is designed to mate with the angled slope of the notch portion 22 on the bottom face 18 of the corresponding battery 10. Both the overhanging rim 50 and the step portion 52 span the entire width of the first end 44 of the battery well 40. The lower surface of the overhanging rim 50 runs substantially parallel to the upper surface of the step portion 52. The distance separating the overhanging rim 50 from the step portion 52 at the first end 44 of the battery well 40 is important, in that the first end 14 of the battery base portion 12 is designed to be closely receivable into this area. A battery having a first end of a larger height or incompatible configuration with the overhanging rim 50 and step portion 52, will not be accepted into the battery well 40.

The first end 44 of each battery well 40 further contains two upright protrusions 54 which extend into the battery well 40 towards the opposite second end 46 of the well. The two protrusions 54 extend the entire height of the first end 44, from the step portion 52 to the overhanging rim 50. The two protrusions 54 are generally parabolic in cross-sectional shape with extended flat surfaces at their apex. The depth of the two protrusions 54 (extending from the first end 44 toward the second end 46 of the well) form a significant portion of the width of the overhanging rim 50 and step portion 52, but do not extend out beyond the end of the overhanging rim 50. If the two protrusions 54 were to extend out beyond the end of the overhanging rim 50, then an embodiment of a second battery 80 (see description below) would not be held in place at the first end 44 of the well 40 and could fall out of the charging unit 42 or portable defibrillator 70.

A blade connector 56 is located at the center of the step portion 52 of each battery well 40. Ideally the blade connector 56 is located symmetrically between the two protrusions 54. The blade connector 56 of each battery well 40 is positioned so that it can interface with the blade connector 26 of a corresponding battery 10, thus allowing communication between the electronic circuitry of the charging unit 42 or portable defibrillator 70 and the circuitry of the preferred embodiment intelligent battery 10.

Figure 8B:
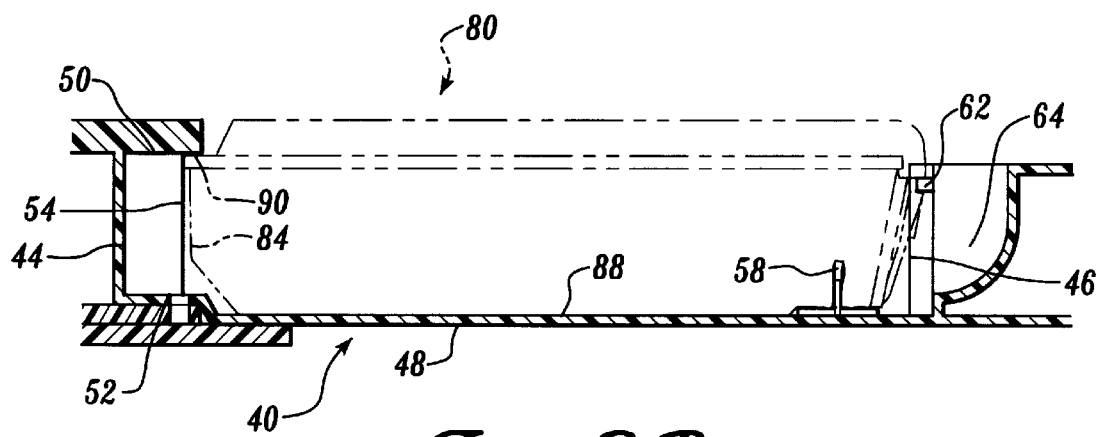
FIG. 8B illustrates a side cross-sectional view of an actual embodiment battery well and a second battery drawn in phantom, with the battery shown located in the battery well such that the at least one protrusion in the first end of the battery well abuts against the substantially flat first end of the battery.
Figure 9:
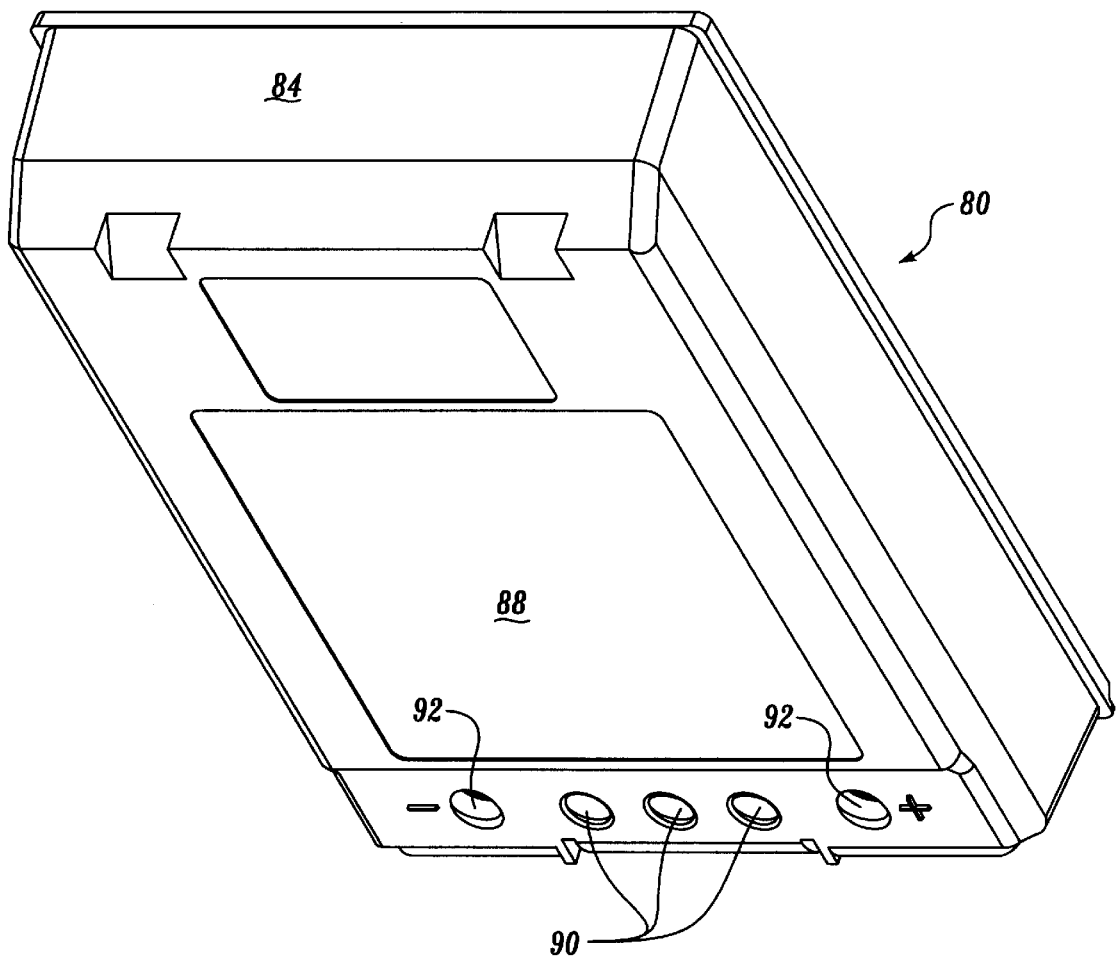
FIG. 9 illustrates a bottom perspective view of a second battery of the present invention having a substantially flat first end and a reduced length relative to the first battery of FIGS. 1–3.
Figure 10:
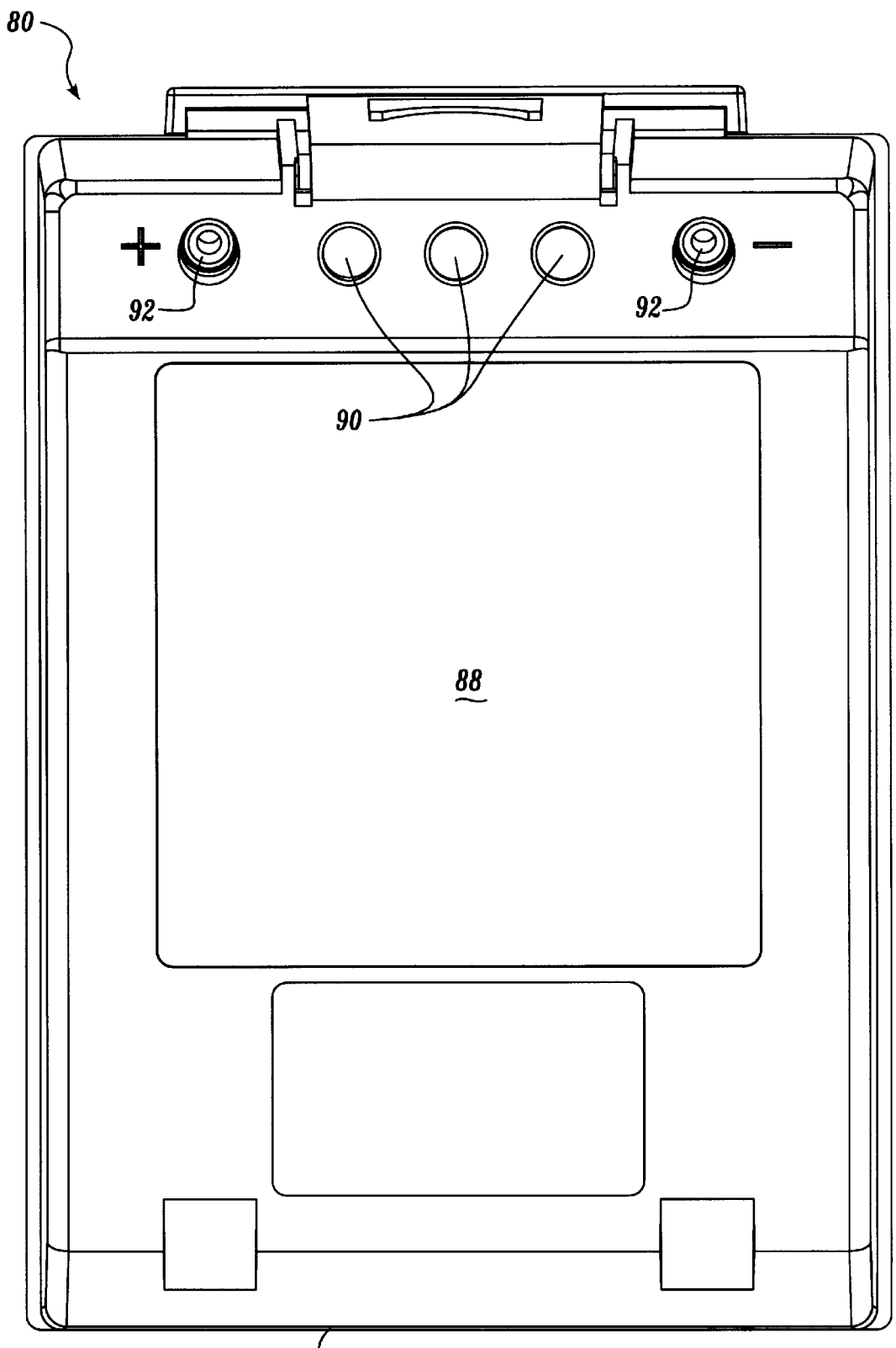
FIG. 10 illustrates a bottom view of the second battery of the present invention having a substantially flat first end and a reduced length relative to the first battery of FIGS. 1–3.

Referring to FIGS. 8A and 8B, the two protrusions 54 incorporated into the first end 44 of each battery well 40 play a specifically designed dual purpose. The battery well 40 with the two protrusions 54 at its first end 44 is designed to accept the above-described actual embodiment first battery 10, which has a length and shape such that the two keyed recesses 24 of the first battery 10 mate with the two protrusions 54 in the first end 44 of the corresponding battery well 40, as shown in FIG. 8A. In this mating position the blade connector 26 of the first battery 10 interfaces with the blade connector 56 of the corresponding battery well 40. However, the battery well 40 is also capable of accepting another embodiment second battery 80 (see FIGS. 9 and 10) that has a shorter length and a substantially flat first end 84. In this second mating condition the substantially flat first end 84 of the shorter length second battery 80 abuts against the two protrusions 54 in the battery well 40, as shown in FIG. 8B. The blade connector 56 of well 40 is not engaged and thus not utilized by the second battery 80.

These alternate methods of battery acceptance allow the battery well 40 to ideally accept an actual embodiment first battery 10 (see FIGS. 1–3) with its incorporated blade connector 26, or in an alternate situation to still be able to accept and utilize a shorter length older design battery 80 (see FIGS. 9 and 10) without the keyed recesses 24 and blade connector 26. This allows the charging unit 42 and portable defibrillator 70 to be backwardly compatible with earlier model batteries 80, but prevents the battery 10 of new design from being placed into an incompatible older design charging unit or portable defibrillator which is not compatible. The battery well 40 does, however, prevent the insertion of any non-compatible older design battery by way of the spacing between the overhanging rim 50 and the raised step portion 52 located therebeneath.

Referring to FIGS. 5–7, the bottom floor 48 of each battery well 40 further contains two banana plug terminals 58, near the second end 46. These banana plug terminals 58 are designed to be received into the two corresponding apertures 28 in the bottom face 18 of the first battery 10 or into the corresponding apertures 92 on the bottom face 88 of the second battery 80. The banana plug terminals 58 are the conductive contacts that connect to the positive and negative terminals of the battery cell. The charging unit 42 uses the banana plug terminals 58 to charge both the first battery 10 and the second battery 80. The batteries 10 and 80 use the banana plug terminals 58 to power the portable defibrillator 70.

The battery wells 40 of the charging unit 42 also contain three retractable contact pins 60 that are linearly aligned and located between the two banana plug terminals 58 on the bottom floor 48 of each well 40 near the second ends 46, as shown in FIGS. 5 and 6. The battery wells 140 of the portable defibrillator 70 do not contain these three retractable contact pins 60, as shown in FIG. 7. Referring again to FIGS. 5 and 6, the retractable contact pins 60 allow the charging unit 42 to interface with a version of an older design battery 80, which contains intelligence circuitry, in the same fashion as the charging unit 42 would with a first battery 10 of newer design using the blade connector 26.

Some older design second batteries 80 also contain electronic circuitry to regulate their charging and conditioning. As shown from FIGS. 9 and 10, this circuitry can be interfaced with by way of three aligned, circular conductive contacts 90 located between two pin receiving apertures 92 in a second battery 80 that are equivalent to the two apertures 28 in the battery 10. The three conductive contacts 90 of an "intelligent" second battery 80 are aligned with the three retractable contact pins 60 in the battery wells 40 of the charging unit 42. This further illustrates the multi-compatibility of the battery wells 40, particularly within the charging unit 42.

The second end 46 of each battery well 40 contains an overhanging flange 62 that is bisected by a central indentation 64. The overhanging flange 62 is designed to hook with the latch member 30 upon insertion of a battery 10, securing the battery in place in the battery well 40. The latch member 30 of the battery 10 can be accessed by way of the central indentation 64 to push the latch member from its extended position into its retracted position, thus detaching the latch member from the overhanging flange 62 and releasing the battery from the battery well. The distal lip 32 provides a gripping edge to help facilitate removing the battery 10 from the well 40.

The present invention has been described in relation to several actual embodiments of the present invention. One of ordinary skill after reading the foregoing specifications, may be able to effect various other changes, alterations, and substitutions or equivalents without departing from the concepts disclosed. It is therefore intended that the scope of the Letters Patent granted hereon be limited only by the definitions contained in the appended claims and equivalents thereof.

The embodiments of the invention in which an exclusive property or privilege is claimed are defined as follows:

1. A battery configured to locate into a receiving battery well, the battery well having opposite first and second ends, a bottom floor spanning between the first and second ends, at least one protrusion formed at the first end of the well and extending toward the second end of the well and an overhang extending along the first end of the well to define a rim portion of the well, the battery comprising:
   (a) a base portion generally in the shape of a rectangular parallelpiped, the base portion defining an opposite first and second end, a bottom face spanning between the first and second ends, and an upper ledge extending along the perimeter of the first end of the base portion opposite the bottom face, and where the distance along the battery base portion from the first end to the second end is defined as the length of the battery base portion, and the distance orthogonal from the bottom face of the base portion to the upper ledge of the base portion is defined as the height of the battery base portion;
   (b) the battery base portion having at least one keyed recess formed in the first end of the base portion and having a shape and length such that the keyed recess is configured to mate with the at least one corresponding protrusion located at the first end of the battery well; and
   (c) the upper ledge of the battery base portion spaced from the bottom face a distance along the height of the base portion such that the upper ledge is closely receivable under the rim portion of the battery well.

2. The battery of claim 1, wherein the bottom face of the battery base portion comprises a raised notch opposite the upper ledge extending along the first end of the base portion to define a notch portion of the battery base portion, that is spaced from the bottom face a distance along the height of the battery base portion such that the notch portion of the battery base portion is closely receivable over a corresponding step portion in the receiving battery well.

3. The battery of claim 1, wherein the at least one recess in the first end of the base portion is formed in the direction of the opposite second end of the battery base portion.

4. The battery of claim 1, wherein the length of the at least one recess formed in the first end, spans the entire height of the battery base portion.

5. The battery of claim 1, wherein the at least one recess formed in the first end of the base portion is configured to be channel shaped.

6. The battery of claim 5, wherein the channel shaped at least one recess formed in the first end of the base portion comprises outwardly sloping sidewalls.

7. The battery of claim 1, wherein the depth of the at least one recess formed in the first end of the battery base portion is a significant portion of the width of the upper ledge in the battery base portion.

8. The battery of claim 1, wherein the battery further comprises conductive contacts that are located within two apertures in the bottom face of the base portion, the apertures being configured to mate with positive and negative terminals of a pin shaped configuration in the receiving battery well.

9. The battery of claim 1, wherein the base portion comprises a blade connector at the intersection of the first end and the bottom face of the base portion, that is configured to interface between a battery's internal circuitry and a corresponding blade connector in the receiving battery well.

10. The battery of claim 1, wherein the battery base portion contains two keyed recesses in the first end of the base portion.

11. The battery of claim 9, wherein the blade connector is located between two keyed recesses in the first end of the base portion.

12. The battery of claim 1, wherein the second end of the base portion defines a latch member that is movable between an extended position wherein the latch member nominally protrudes from the base portion, and a retracted position wherein the latch member does not protrude from the base portion.

13. The battery of claim 12, wherein the nominally protruding latch member comprises a lip at its distal portion.

14. The battery of claim 12, wherein the nominally protruding latch member is resiliently attached to the second end of the battery base portion.

15. A battery well, configured to receive a battery, the battery having a base portion defining opposite first and second ends, a bottom face spanning between the first and second ends, and an upper ledge extending along the perimeter of the first end of the base portion opposite the bottom face, the well comprising:
   (a) a cavity generally in the shape of a rectangular parallelpiped, the well defining an opposite first and second end, a bottom floor spanning between the first and second ends, and an overhang extending along the first end of the well to define a rim portion of the well, and where the distance along the well from the first end to the second end is defined as the length of the battery well, and the distance orthogonal from the bottom floor of the well to the rim portion is defined as the depth of the battery well; and
   (b) at least one protrusion formed at the first end of the well and extending toward the second end of the well, the well thereby accepting
      a first battery having at least one corresponding keyed recess formed in the first end of the battery base portion and having a shape and length such that the keyed recess is configured to mate with the at least one protrusion located at the first end of the battery well; and,
      a second battery having a battery base portion forming a substantially flat first end and having a shape and length that includes a shorter length than the first battery such that the substantially flat first end of the second battery is configured to abut against the at least one protrusion located at the first end of the battery well.

16. The battery well of claim 15, wherein the overhanging rim portion of the battery well is spaced from the bottom floor a distance along the depth of the battery well such that the upper ledge of the battery base portion is closely receivable under the overhanging rim portion of the battery well, and thereby preventing insertion of a battery with a base portion of a greater depth.

17. The battery well of claim 15, wherein the bottom floor of the battery well comprises a raised step opposite the overhanging rim portion extending along the first end of the well to define a step portion of the battery well, that is spaced from the bottom floor a distance along the depth of the battery well such that a battery base portion comprising a corresponding notch portion in the bottom face of the base portion, is closely receivable over the step portion of the battery well, and thereby preventing insertion of a battery comprising a base portion without a corresponding notch portion.

18. The battery well of claim 15, wherein the length of the at least one protrusion formed at the first end of the well extends from the bottom floor of the battery well to the overhanging rim portion.

19. The battery well of claim 15, wherein the at least one protrusion in the first end of well is configured to form a substantially parabolic projection further comprising an extended substantially flat surface facing the direction of the opposite second end of the battery well.

20. The battery well of claim 15, wherein the at least one protrusion formed at the first end of the well extends towards the second end of the well a shorter distance than the overhanging rim portion extends towards the second end of the well.

21. The battery well of claim 15, wherein the width of the at least one protrusion formed in the first end of the battery well is a significant portion of the width of the overhanging rim portion of the battery well.

22. The battery well of claim 15, wherein the battery well comprises two protrusions formed at the first end of the well that extend towards the second end of the well.

23. The battery well of claim 15, wherein the battery well comprises a blade connector at the intersection of the first end and the bottom floor of the well, that is configured to interface with a corresponding blade connector in the corresponding battery.

24. The battery well of claim 22, wherein the blade connector is located between two protrusions formed at the first end of the well.

25. The battery well of claim 15, wherein the well further comprises a positive and a negative terminal of pin shaped configurations that are located on the bottom floor of the battery well near the second end, the pin shaped terminals being design to mate in receiving apertures in the bottom face of the corresponding battery.

26. The battery well of claim 15, wherein the well further comprises a plurality of contact points for interfacing with the electronic circuitry of a compatible battery.

27. The battery well of claim 26, wherein the well further comprises a plurality of retractable contacts for interfacing with the electronic circuitry of a compatible battery.

28. The battery well of claim 27, wherein the well further comprises a plurality of retractable pin shaped contacts for interfacing with the electronic circuitry of a compatible battery.

29. The battery well of claim 28, wherein the well further comprises three retractable pin shaped contacts for interfacing with the electronic circuitry of a compatible battery.

30. The battery well of claim 29, wherein the well further comprises three retractable pin shaped contacts linearly aligned on the bottom floor of the well near the second end, for interfacing with the electronic circuitry of a compatible battery.

31. The battery well of claim 30, wherein the well further comprises three retractable pin shaped contacts linearly aligned on the bottom floor of the well near the second end, between the positive and negative pin shaped terminals, for interfacing with the electronic circuitry of a compatible battery.

32. The battery well of claim 15, wherein the top of the second end of the well further comprises an overhanging flange configured to be used in operative association with a latch member of a corresponding battery.

33. The battery well of claim 15, wherein the second end of the well further comprises an indentation thereby allowing access a latch release mechanism.

34. A battery configured to locate into a receiving battery well, the battery well having opposite first and second ends, a bottom floor spanning between the first and second ends, an indexing means formed at the first end of the well and an overhang extending along the first end of the well to define a rim portion of the well, the battery comprising:

(a) a base portion generally in the shape of a rectangular parallelpiped, the base portion defining an opposite first and second end, a bottom face spanning between the first and second ends, and an upper ledge extending along the perimeter of the first end of the base portion opposite the bottom face, and where the distance along the base portion from the first end to the second end is defined as the length of the battery base portion, and the distance orthogonal from the bottom face of the base portion to the upper ledge of the base portion is defined as the height of the battery base portion;

(b) the battery base portion containing an indexing means formed in the first end of the base portion and having a shape and length such that the indexing means is configured to mate with a corresponding indexing means located at the first end of the battery well; and (c) the upper ledge of the battery base portion spaced from the bottom face a distance along the height of the base portion such that the upper ledge is closely receivable under the rim portion of the battery well.

\* \* \* \* \*

UNITED STATES PATENT AND TRADEMARK OFFICE
CERTIFICATE OF CORRECTION

PATENT NO. : 6,127,063    Page 1 of 2
DATED : October 3, 2000
INVENTOR(S) : L.W. Kowalsky et al.

It is certified that error appears in the above-identified patent and that said Letters Patent is hereby corrected as shown below:

| COLUMN | LINE | |
|---|---|---|
| [56] Pg. 1, col. 1 | Refs. Cited (Other Publs., Item 1) | "LIFEPACK®" should read --LIFEPAK®-- |
| 10 (Claim 15, | 47 line 19) | "accepting" should read --accepting:-- |
| 10 (Claim 15, | 53 line 25) | "and," should read --and-- |
| 11 (Claim 25, | 45 line 5) | "design" should read --designed-- |
| 11 (Claim 27, | 50 line 1) | "26," should read --15,-- |
| 12 (Claim 28, | 1 line 1) | "27," should read --15,-- |
| 12 (Claim 29, | 5 line 1) | "28," should read --15,-- |
| 12 (Claim 30, | 8 line 1) | "29," should read --15,-- |

UNITED STATES PATENT AND TRADEMARK OFFICE
CERTIFICATE OF CORRECTION

PATENT NO. : 6,127,063
DATED : October 3, 2000
INVENTOR(S) : L.W. Kowalsky et al.

It is certified that error appears in the above-identified patent and that said Letters Patent is hereby corrected as shown below:

COLUMN      LINE

12              13          "30," should read --15,--
(Claim 31, line 1)

12              23          "indentation thereby" should read --indentation,
(Claim 33, line 2)          thereby--

Signed and Sealed this

First Day of May, 2001

Attest:

NICHOLAS P. GODICI

*Attesting Officer*     *Acting Director of the United States Patent and Trademark Office*